United States Patent
Hughes (10) Patent No.: US 8,636,919 B1
(45) Date of Patent: *Jan. 28, 2014

(54) REACTIVE SOLUTIONS

(76) Inventor: Kenneth D. Hughes, Alpharetta, GA (US)

( * ) Notice: Subject to any disclaimer, the term of this patent is extended or adjusted under 35 U.S.C. 154(b) by 759 days.

This patent is subject to a terminal disclaimer.

(21) Appl. No.: 11/089,682

(22) Filed: Mar. 25, 2005

Related U.S. Application Data (60) Provisional application No. 60/557,146, filed on Mar. 26, 2004.

(51) Int. Cl.
*A62D 3/00* (2007.01)
*A61L 9/00* (2006.01)

(52) U.S. Cl.
USPC ......................................... 252/186.1; 422/29

(58) Field of Classification Search
USPC ......................................... 422/29; 252/186.1
See application file for complete search history.

(56) References Cited

U.S. PATENT DOCUMENTS

| | | |
|---|---|---|
| 286,370 A | 10/1883 | Baker |
| 3,238,056 A | 3/1966 | Pall et al. |
| 3,344,061 A | 9/1967 | Kellum |
| 3,375,933 A | 4/1968 | Rodman |
| 3,442,796 A | 5/1969 | Hayes |
| 3,545,622 A | 12/1970 | Sakhonvsky |
| 3,662,893 A | 5/1972 | Humbert |
| 3,871,881 A | 3/1975 | Mikelsons |
| 3,996,131 A | 12/1976 | Conn |
| 4,078,112 A | 3/1978 | Bibeau |
| 4,079,001 A | 3/1978 | Haase et al. |
| 4,084,747 A | 4/1978 | Alliger |
| 4,098,690 A | 7/1978 | Semmens |
| 4,160,727 A | 7/1979 | Harris |
| 4,167,479 A | 9/1979 | Besik |
| 4,178,361 A | 12/1979 | Cohen et al. |
| 4,182,676 A | 1/1980 | Casolo |
| 4,190,576 A | 2/1980 | Thomson et al. |
| 4,194,040 A | 3/1980 | Breton et al. |
| 4,198,296 A | 4/1980 | Doumas et al. |
| 4,230,595 A | 10/1980 | Yamaji et al. |
| 4,251,224 A | 2/1981 | Cowley et al. |
| 4,252,571 A | 2/1981 | Reilly |
| 4,282,094 A | 8/1981 | Mitchell |
| 4,330,531 A | 5/1982 | Alliger |
| 4,482,459 A | 11/1984 | Shiver |
| 4,585,482 A | 4/1986 | Tice et al. |
| 4,610,790 A | 9/1986 | Reti et al. |
| 4,623,467 A | 11/1986 | Hamlin |
| 4,629,464 A | 12/1986 | Takata et al. |
| 4,642,192 A | 2/1987 | Heskett |

(Continued)

FOREIGN PATENT DOCUMENTS

| | | |
|---|---|---|
| FR | 2790767 A1 | 9/2000 |
| JP | 59145087 A | 8/1984 |
| JP | 62204892 | 9/1987 |
| JP | 2000211901 | 8/2000 |
| WO | WO 99/26987 | 6/1999 |

(Continued)

*Primary Examiner* — Kevin Joyner
(74) *Attorney, Agent, or Firm* — F. Brent Nix; Johnson, Marcou & Isaacs (57) ABSTRACT

Material and methods are disclosed involving the generation and containment of solutions incorporating reactive precursors and reactive treatment agents. Formulations of these materials can be applied widely as disinfectants, odor control agents, decontamination and fumigation agents, liquid, gas, and air treatment materials, respiratory agents, food and beverage processing agents, neutralization agents, and in many industrial, residential, medical and military surface treatment operations.

14 Claims, 1 Drawing Sheet

(56) References Cited

U.S. PATENT DOCUMENTS

| | | |
|---|---|---|
| 4,643,182 A | 2/1987 | Klein |
| 4,645,503 A | 2/1987 | Lin et al. |
| 4,645,604 A | 2/1987 | Martinola et al. |
| 4,670,150 A | 6/1987 | Hsiung et al. |
| 4,683,039 A | 7/1987 | Twardowski et al. |
| 4,702,836 A | 10/1987 | Mutoh et al. |
| 4,711,723 A | 12/1987 | Bray |
| 4,717,566 A | 1/1988 | Eckenhoff et al. |
| 4,806,244 A | 2/1989 | Guilhern |
| 4,851,122 A | 7/1989 | Stanley |
| 4,865,733 A | 9/1989 | Tsuru et al. |
| 4,874,511 A | 10/1989 | Kawasaki et al. |
| 4,880,541 A | 11/1989 | Chiron et al. |
| 4,889,630 A | 12/1989 | Reinhardt et al. |
| 4,900,444 A | 2/1990 | Seita et al. |
| 4,902,427 A | 2/1990 | Szczepanik |
| 4,946,603 A | 8/1990 | Laugharn et al. |
| 4,988,440 A | 1/1991 | Bernard et al. |
| 5,019,311 A | 5/1991 | Koslow |
| 5,071,610 A | 12/1991 | Hagen et al. |
| 5,082,568 A | 1/1992 | Holler |
| 5,085,781 A | 2/1992 | Tsuru et al. |
| 5,089,119 A | 2/1992 | Day et al. |
| 5,116,415 A | 5/1992 | Rinehart |
| 5,118,655 A | 6/1992 | Pedersen |
| 5,122,274 A | 6/1992 | Heskett |
| 5,126,070 A | 6/1992 | Leifheit et al. |
| 5,127,411 A | 7/1992 | Schoolman et al. |
| 5,135,654 A | 8/1992 | Heskett |
| 5,143,752 A | 9/1992 | Nakajima et al. |
| 5,147,722 A | 9/1992 | Koslow |
| 5,149,437 A | 9/1992 | Wilkinson et al. |
| 5,156,739 A | 10/1992 | Dawson et al. |
| 5,161,686 A | 11/1992 | Weber et al. |
| 5,180,491 A | 1/1993 | Polasky |
| 5,189,092 A | 2/1993 | Koslow |
| 5,198,118 A | 3/1993 | Heskett |
| 5,205,928 A | 4/1993 | Inove et al. |
| 5,215,657 A | 6/1993 | Goldfield et al. |
| 5,238,574 A | 8/1993 | Kawashima et al. |
| 5,249,948 A | 10/1993 | Koslow |
| 5,266,203 A | 11/1993 | Mukhopadhyay et al. |
| 5,271,848 A | 12/1993 | Smith et al. |
| 5,298,205 A | 3/1994 | Hayes et al. |
| 5,331,037 A | 7/1994 | Koslow |
| 5,338,766 A | 8/1994 | Phan et al. |
| 5,346,565 A | 9/1994 | White |
| 5,360,609 A | 11/1994 | Wellinghoff |
| 5,384,047 A | 1/1995 | Scheckler et al. |
| 5,415,759 A | 5/1995 | Cawlfield et al. |
| 5,422,340 A | 6/1995 | Ammann et al. |
| 5,482,773 A | 1/1996 | Bair |
| RE35,267 E | 6/1996 | Tsuru et al. |
| 5,552,046 A | 9/1996 | Johnston et al. |
| 5,580,749 A | 12/1996 | Hughes |
| 5,589,066 A | 12/1996 | Gray |
| 5,597,487 A | 1/1997 | Vogel et al. |
| 5,635,071 A | 6/1997 | Al-Samadi |
| 5,650,446 A | 7/1997 | Wellinghoff et al. |
| 5,651,884 A | 7/1997 | Ichitsuka et al. |
| 5,656,140 A | 8/1997 | Oesterle et al. |
| 5,670,053 A | 9/1997 | Collentro et al. |
| 5,676,745 A | 10/1997 | Kelly et al. |
| 5,681,447 A | 10/1997 | Maycock et al. |
| 5,688,378 A | 11/1997 | Khoe et al. |
| 5,728,157 A | 3/1998 | Prescott |
| 5,750,026 A | 5/1998 | Gadkaree et al. |
| 5,755,969 A | 5/1998 | Okamoto |
| 5,770,416 A | 6/1998 | Lihme et al. |
| 5,792,513 A | 8/1998 | Koslow et al. |
| 5,855,861 A * | 1/1999 | Lee ................ 423/477 |
| 5,866,003 A | 2/1999 | Okubo et al. |
| 5,882,517 A | 3/1999 | Chen et al. |
| 5,935,887 A | 8/1999 | Sudo et al. |
| 5,961,843 A | 10/1999 | Hayakawa et al. |
| 5,977,003 A | 11/1999 | Wilshaw et al. |
| 5,997,829 A | 12/1999 | Sekine et al. |
| 6,051,135 A | 4/2000 | Lee et al. |
| 6,054,050 A | 4/2000 | Dyke |
| 6,054,059 A | 4/2000 | Latimer, Jr. et al. |
| 6,103,125 A | 8/2000 | Kuepper |
| 6,110,375 A | 8/2000 | Bacchus et al. |
| 6,117,333 A | 9/2000 | Frankiewicz et al. |
| 6,156,186 A | 12/2000 | Mueller et al. |
| 6,162,361 A | 12/2000 | Adiga |
| 6,180,016 B1 | 1/2001 | Johnston et al. |
| 6,187,192 B1 | 2/2001 | Johnston et al. |
| 6,190,556 B1 | 2/2001 | Uhlinger |
| 6,197,193 B1 | 3/2001 | Archer |
| 6,203,688 B1 | 3/2001 | Lipsztajn et al. |
| 6,238,643 B1 | 5/2001 | Thangaraj et al. |
| 6,274,041 B1 | 8/2001 | Williamson et al. |
| 6,284,152 B1 * | 9/2001 | Kross .................. 252/187.21 |
| 6,290,686 B1 | 9/2001 | Tanzer |
| 6,312,598 B1 | 11/2001 | Munson et al. |
| 6,355,093 B1 | 3/2002 | Schwartz et al. |
| 6,368,510 B2 | 4/2002 | Friot |
| 6,376,011 B1 | 4/2002 | Reeves et al. |
| 6,395,678 B1 | 5/2002 | Summers et al. |
| 6,428,696 B2 | 8/2002 | Kuke |
| 6,432,322 B1 | 8/2002 | Speronello et al. |
| 6,451,253 B1 | 9/2002 | Pitochelli et al. |
| 6,458,162 B1 | 10/2002 | Kovlish et al. |
| 6,458,735 B1 | 10/2002 | Klatte |
| 6,461,514 B1 | 10/2002 | Al-Samadi |
| 6,464,672 B1 | 10/2002 | Buckley |
| 6,468,942 B1 | 10/2002 | Sansalone |
| 6,503,419 B2 | 1/2003 | Klatte |
| 6,552,141 B1 | 4/2003 | Chmelir et al. |
| 6,575,961 B2 | 6/2003 | Joshi |
| 6,605,304 B1 * | 8/2003 | Wellinghoff et al. ........ 424/489 |
| 6,607,668 B2 | 8/2003 | Rela |
| 6,677,256 B1 | 1/2004 | Sun et al. |
| 6,712,974 B1 | 3/2004 | Palm et al. |
| 6,764,661 B1 | 7/2004 | Girard |
| 6,790,427 B2 | 9/2004 | Charles et al. |
| 6,794,318 B2 * | 9/2004 | Anderson et al. ............ 442/123 |
| 6,821,435 B1 | 11/2004 | Lindquist et al. |
| 6,833,075 B2 | 12/2004 | Hughes |
| 6,861,002 B2 | 3/2005 | Hughes |
| 6,878,285 B2 | 4/2005 | Hughes |
| 6,957,743 B2 | 10/2005 | Johnston et al. |
| 7,172,646 B2 | 2/2007 | Tempel et al. |
| 7,201,841 B2 | 4/2007 | Hughes |
| 7,229,647 B2 | 6/2007 | Lee et al. |
| 7,383,946 B2 | 6/2008 | Hughes |
| 2002/0006427 A1 | 1/2002 | Umezu et al. |
| 2002/0158007 A1 | 10/2002 | Li |
| 2003/0015467 A1 | 1/2003 | Johnston et al. |
| 2003/0044314 A1 * | 3/2003 | Aamodt et al. ................ 422/29 |
| 2003/0118503 A1 | 6/2003 | Pu et al. |
| 2003/0135181 A1 * | 7/2003 | Chen et al. .................. 604/374 |
| 2003/0173287 A1 | 9/2003 | Johnston et al. |
| 2003/0196955 A1 | 10/2003 | Hughes |
| 2003/0196959 A1 | 10/2003 | Hughes |
| 2003/0196960 A1 | 10/2003 | Hughes |
| 2003/0196966 A1 | 10/2003 | Hughes |
| 2004/0149571 A1 * | 8/2004 | Tremblay et al. .......... 204/275.1 |
| 2004/0149634 A1 | 8/2004 | Hughes |
| 2004/0159605 A1 | 8/2004 | Hughes |
| 2004/0232068 A1 | 11/2004 | Johnson et al. |
| 2005/0033251 A1 * | 2/2005 | Toreki et al. ................ 604/367 |
| 2005/0079230 A1 * | 4/2005 | Lee et al. ..................... 424/661 |
| 2005/0098495 A1 | 5/2005 | Hughes |
| 2006/0060818 A1 | 3/2006 | Tempel et al. |
| 2006/0289349 A1 | 12/2006 | Hughes |

FOREIGN PATENT DOCUMENTS

| | | |
|---|---|---|
| WO | WO 02/30766 | 4/2002 |
| WO | WO 2004/071960 A2 | 8/2004 |

* cited by examiner

REACTIVE SOLUTIONS

CROSS-REFERENCE TO RELATED APPLICATION

This application claims priority to and the benefit of the filing date of U.S. provisional application Ser. No. 60/557,146, entitled "Reactive Solutions," filed on Mar. 26, 2004, which is entirely incorporated herein by reference.

FIELD OF THE INVENTION

The herein disclosed invention is directed at the generation and containment of solutions incorporating reactive gases and their precursors. These solutions and formulations can be applied widely as disinfectants, odor control agents, decontamination and fumigation agents, liquid, gas, and air treatment materials, respiratory agents, food and beverage processing agents, neutralization agents, and in many industrial, residential, medical and military surface treatment operations.

BACKGROUND OF THE INVENTION

Over time the concentration of contaminants associated with porous and nonporous surfaces, and in fluids such as gases, liquids, and solutions, usually increases. In many consumer and industrial applications the concentration of these contaminants needs to be reduced before the surface or fluid is utilized. Many different technologies have been developed to accomplish this goal. In the treatment of surfaces, highly reactive chemical agents are often used. Preferred chemical agents provide intimate contact with all aspects of the surface. In the treatment of fluids, such as gases, liquids, and solutions, two dominant and significantly different strategies exist. The first strategy involves passing the fluid through filters and filtration devices which contain filters. In this strategy, contaminants are retained in the filter as the fluid passes through the filter. The second strategy involves the use of highly reactive chemical agents to decrease the concentration of contaminants. In this strategy, the chemical agents are introduced directly into the fluid, from a concentrated source. Many highly reactive chemical agents are regulated as pesticides and require specialized handling. The use of highly reactive chemical agents in many surface and fluid treatment applications is usually less costly, less complicated, and less time consuming than installing filters and filtration devices.

This invention does not involve the use of fluid filters or purification devices for gases, water, and other aqueous liquids, which remove contaminants from the gas, water, or other aqueous liquid passing through them.

This invention does involve the generation, storage, and delivery of highly reactive chemical agents to surfaces and to fluids such as gases, liquids, and solutions. Preferred highly reactive chemical agents of this invention are gases.

The unique and beneficial characteristics of gases such as chlorine dioxide, oxygen, sulfur dioxide, carbon dioxide, chlorine, and nitrogen containing gases are well known in many fields. These gases modify solution properties by interacting with both chemical and biological components contained therein. Methods for generating and packaging many reactive gases for transportation and for storage on-site when continual use is required have been extensively described. However, a particular distinction must be made with respect to chlorine dioxide gas generation, storage, and transport. Although this reactive gas has many beneficial characteristics, its generation is hazardous, it can not be packaged or stored safely, and therefore it can not be transported to or stored at the site of application. As a result, this highly versatile gas has been difficult to utilize in many small volume, low concentration applications, and by consumers in residential applications.

The instant invention provides novel materials and methods for safely, economically, and efficiently generating, containing, and utilizing chlorine dioxide gas in a wide range of concentrations. The instant invention facilitates the fabrication and wide dissemination of many new consumer, medical, industrial, and military useful materials and products which facilitate the direct introduction of highly reactive chemical agents onto surfaces and into fluids. The materials and methods are applicable to many other reactive gases including, sulfur dioxide, carbon dioxide, chlorine, oxygen, and gases which contain nitrogen as well as carrier solutions including polar and nonpolar liquids. The materials of the invention are widely and immediately available and the methods of the invention are extremely simple, allowing wide spread dissemination of products based upon the invention.

DESCRIPTION OF RELATED ART

Safe, convenient, batch mode preparation of small volumes of chlorine dioxide gas, sulfur dioxide, carbon dioxide, chlorine, gases which contain nitrogen, and other reactive gases continues to receive the attention and interest of many product development groups. While carbon dioxide and sulfur dioxide as well as nitrogen containing gases are easily stored and transported, the requirements for storage and transport of chorine dioxide precursor reagents, as well as generation of the gas, are much more complicated. Chlorine dioxide is commonly generated in batch mode through the mixing of metal chlorite and acidic solutions or solutions containing chlorine-based oxidizers. Chlorine dioxide can be generated continuously through use of both chlorite and chlorate salts and mixing or electrochemical equipment.

The patent literature and prior art associated with the storage of chlorine dioxide precursor reagents, and the generation of chlorine dioxide gas can be separated into three distinct arenas. The first arena contains description and application of mechanical devices and their methods of use. These mechanical devices target the controlled mixing and reaction of chlorine dioxide precursor reagents, separation of the product gas from the reaction solution, increasing the efficiency of reagent use, and ultimately controlling the delivery of gas into a liquid or gas phase system. Example art in this arena can be found in the following U.S. Pat. Nos. 4,683,039, 6,428,696, 6,203,688, 5,415,759, and 114,757.

The second arena contains description and application of powdered materials which contain all or some of the chlorine dioxide precursor reagents and their methods of use. These chemical systems target the protective storage of the precursor reagents, the mechanism of exposure of the dry powder and precursor reagents to water, and the interaction of the powdered components and precursor reagents with activators, to generate chlorine dioxide. Important considerations in the design of these powdered systems include the concentration of precursor reagents, the stability of the precursor reagents, the need for activating agents, sensitivity to liquid and vapor water, and the rate and duration at which chlorine dioxide gas can be generated. In the majority of powdered and compressed powder systems silicates, zeolites, and desiccants are used to carry the precursor reagents for generating chlorine dioxide and for protecting the reagents from water. Many preparations require spray drying or other rapid means of removing water from the precursor reagents. Exposure to water often initiates reactions yielding chlorine dioxide gas. Much of this prior art requires sophisticated control of materials, chemical reagents, and powder processing technical know-how and specialized packaging. These requirements limit the range of gas concentrations that can be generated, the rate and duration of gas release, and ultimately the types of applications that can be addressed with these materials. Exemplary art in the field include the following U.S. Pat. Nos. 6,238,643, 6,432,322, 21,819, 6,605,304, 4,585,482, 6,503, 419, and 6,458,735.

The third arena involves the use of solutions which contain the precursor reagents for chlorine dioxide generation. These solutions are often referred to as stabilized chlorine dioxide and usually consist of an aqueous solution of sodium chlorite with an alkaline pH. Exposure of these solutions to an activator, a powdered or aqueous acid solution, yields chlorine dioxide gas. Packets of liquid and powdered reagents are usually combined in a large volume vessel and then diluted with water for application. Manipulation of concentrated solutions containing both precursor reagents and the reactive gas require extreme care and thus many products utilize dilute solutions of reagents. Additionally, viscous solutions of stabilized chlorine dioxide precursor reagents and/or chlorine dioxide gas containing solutions have been described. These viscous solutions are prepared through the addition of polymer additives commonly used in the food and cosmetic industries. These highly viscous materials while suitable for niche applications such as skin lotions are inconvenient and difficult to use in many atmospheric, liquid and solid surface treatment applications. Exemplary art in the field include the following U.S. Pat. Nos. 4,084,747, 4,330,531, and 6,451,253.

There continues to be a need for new materials and methods for generating reactive gases, materials and methods which facilitate the storage and transport of gas precursor reagents, as well as materials and methods which facilitate the preparation of secondary solutions which contain a wide range of reactive gas concentrations. Additionally, there is a need for producing consumer friendly products which allow for the safe and inexpensive application of highly reactive chemical agents.

SUMMARY OF THE INVENTION

The invention disclosed involves the controlled generation, storage, and delivery of reactive gases such as chlorine dioxide, sulfur dioxide, carbon dioxide, oxygen, chlorine, and nitrogen containing gases, as well as other reactive gases through the use of particles, fibers, or a combination thereof, which have the capacity to retain and control liquids containing dissolved gases. By understanding and utilizing the physical and chemical properties of the liquids, gases, and particulates, fibers, or combinations thereof, which have the capacity to adsorb and absorb liquids, a wide range of highly reactive surface and fluid treatment material compositions can be generated. These compositions which contain liquids, solids, and gases are easily tuned or tailored for general as well as very specific applications. As example, a composition can be prepared with solids, liquid, and dissolved gas such that individual particles may be manipulated and delivered to a surface or to a fluid, thus delivering a controlled mass of reactive treatment agent. Preferred particles, fibers or combinations thereof, of the invention, control both gas precursor reagents and the generated gas.

Particles, fibers or combinations thereof, of the invention, containing liquids carrying dissolved gases may be used directly in treating surfaces or fluids through intimate contact of the particles, fibers or combinations thereof or indirectly through transfer of the particle or fibers to a secondary solution, where the particles, fibers or combinations thereof, of the invention, release the active treatment agent. This secondary solution is subsequently used to treat a surface or fluid.

Liquids with dissolved highly reactive treatment gases carried by particles, fibers or combinations thereof, of the invention, may be further mixed with adsorbent particles or fibers to provide unique surface and fluid treatment composite materials. These particulate composites provide treatment of a wide range of contaminants associated with surfaces and contaminants dissolved or suspended in fluids.

In many applications, particles, fibers or combinations thereof, of the invention are placed in direct contact with a surface and further manipulated on the surface with an applicator. Exemplary applicators include woven and nonwoven materials.

In fluid treatment applications particles, fibers or combinations thereof, of the invention, can be placed into a container which allows the highly reactive treatment agent to be delivered into the contaminated fluid without bulk transfer of the liquid control particles, fibers or combinations thereof. When using a container or housing for the particles, fibers or combinations thereof, of the invention, the contaminated fluid undergoing treatment does not pass through the container or particles, fibers or combinations thereof, of the invention, in such a manner that provides any filtration or removal of suspended material. This design avoids fouling and unwanted interactions, of particles, fibers or combinations thereof, of the invention. In preferred designs, bulk liquid contained by particles, fibers or combinations thereof, of the invention is not transferred to the contaminated liquid undergoing treatment. In many gas treatment applications, containers used to house the particles, fibers or combinations thereof, of the invention, are designed in a manner to deliver the reactive treatment gas to the contaminated bulk gas through chemical concentration and pressure gradients. Those experienced in the art will understand the wide range of materials available and the gas and liquid transfer and transport characteristics of these materials and the advantages and disadvantages associated with use of these materials in fabricating containers and housings that are not fouled by suspended contaminants.

Particles, fibers or combinations thereof, of the invention, which carry liquids and dissolved reactive gases can be designed for rapid release of the treatment agent or slow release that occurs over extended time periods. Those experienced in the art will understand the chemical and physical characteristics of system components involved in the generation, storage, and delivery of reactive gases in addressing different applications. Preferred embodiments of the invention allow the safe use of these gases by consumers and those who are not expert in surface and fluid treatment operations. Further, preferred embodiments of the invention allow all known uses of chlorine dioxide, sulfur dioxide, carbon dioxide, oxygen, chlorine, and nitrogen containing gases to be accessed. Furthermore, it facilitates the use of these gases for all currently known and anticipated applications now in review by agencies such as the USEPA, FDA, and USDA. It is anticipated that materials and methods of the invention will facilitate the development and approval of many new applications of these reactive treatment agents for consumer, industrial, medical, and military treatment operations.

As the utility of the materials and methods of this invention are far reaching and provide significant benefits that have not been previously described in the field of reactive gas generation, manipulation, and application, there are numerous objects of this invention. Those objects described herein are to be viewed as exemplary.

It is therefore an object of the invention to treat aqueous solutions such as potable water and beverages with concentrations of reactive gases such as chlorine dioxide, carbon dioxide, oxygen, sulfur dioxide, chlorine containing gases, nitrogen containing gases, and other reactive gases such that the liquid obtains a greater degree of purity, through the reduction of biological and chemical contaminants, without the need for filters or filtration technologies which involve passing fluids through filter elements.

It is also an object of the invention to treat solutions used as beverages with concentrations of reactive gases such as chlorine dioxide, carbon dioxide, sulfur dioxide, chlorine containing gases, nitrogen containing gases, and other reactive gases and in combination such that the fluid is modified in a manner which improves the taste and aesthetic qualities without the need for filters or filtration technologies which involve passing fluids through filter elements.

It is a further object of this invention to treat fluids including waste water and industrial water such as cooling and boiler water for chemical and biological contaminants using reactive gases such as chlorine dioxide, carbon dioxide, sulfur dioxide, chlorine containing gases, nitrogen containing gases, and other reactive gases, as well as in combination with other treatment agents such as corrosion inhibitors, flocculating agents, and water quality enhancers without the need for passing the fluid through filters or using filtration technology.

It is an object of this invention to provide a material and method for preparing porous and hard surface cleaning solutions, and decontaminating solutions capable of treating contaminants of significant interest to consumers, industry and the military. Porous materials such as membranes and materials containing natural fibers which require cleaning and sanitizing are objects of this invention.

Further, it is an object of this invention to provide unique laundry formulations that contain reactive gases such as chlorine dioxide, carbon dioxide, sulfur dioxide, chlorine containing gases, nitrogen containing gases, and other reactive gases, as well as in combination with other treatment agents such as surfactants, stain inhibitors, fragrance agents, and other water quality and fabric maintenance enhancers.

It is an object of this invention to treat gaseous systems such as the local atmosphere, enclosed environments, ventilation systems, and breathing air for chemical and biological contaminants, without the need for passing the fluid through filters or using filtration technology.

It is a further object of the invention to provide materials and methods for treating local atmospheres for odors, by consumers in homes, and in many industries such as waste treatment, animal processing, petroleum development, and in medical and health facilities, without the need for passing the fluid through filters or using filtration technology.

Still further it is an object of this invention to provide materials that can be used for the sterilization of liquid and solid materials associated with hospital, medical, surgical, and dental use, without the need for passing the fluid through filters or using filtration technology.

Another object of the invention is to prepare materials which can be used in the treating of wounds (bandages and dressings), and as topical agents in the treatment of skin conditions.

Still further it is an object of this invention to prepare a material that can treat through absorption and solidification biological and medical wastes, as example wastes containing animal fluids.

Another object of the invention is to treat non-aqueous solutions or liquids such as fuels which are contaminated with water, biological and chemical components, without the need for passing the fluid through filters or using filtration technology.

Another object of the invention is to provide materials which are capable of temporarily storing reactive gases and which can be used with devices that can be used once and discarded. Examples of such devices include those associated with preparing drinking water, treating odors, packaging and transporting and storing foods and beverages.

It is another object of this invention to provide a material that can simultaneous generate a reactive gas and absorb and adsorb a liquid spill or loose powder.

Similarly it is an object of this invention to provide a material and method for simultaneously applying a reactive gas and absorbing juices associated with the preparation, delivery, and storage of food and nutritional products.

Another object of the invention is to provide materials and devices for personal hygiene use such as diapers, incontinence products, and feminine care products.

Another object of the invention is to provide a material capable of absorbing and neutralizing liquids and powders contaminated with chemical and biological warfare agents. Likewise it is an object of the invention to provide materials that can efficiently treat solid and porous surfaces that are contaminated with a wide variety of agents.

Further, it is an object of this invention to provide materials for treating recreational water systems, such as pools and spas for chemical and biological contaminants and for preventing biological contamination using reactive gases such as chlorine dioxide, carbon dioxide, sulfur dioxide, chlorine containing gases, nitrogen containing gases, and other reactive gases, as well as in combination with other treatment agents such as corrosion inhibitors, flocculating agents, and water quality enhancers, without the need for passing the fluid through filters or using filtration technology.

Furthermore, it is an object of this invention to produce materials which can incorporate color indicators for visualizing the concentration of the reactive gases, dissolved reagents, and contaminants and for ascertaining the remaining lifetime of the products that incorporate the materials of the invention.

It is also an object of this invention to provide a material that relates gas concentration to surrounding temperature and pressure characteristics.

DETAILED DISCUSSION

Reactive and inert gases have found significant utility in modern society. As a result, significant effort has been expended in the development of methods to isolate, concentrate, store, and transport highly purified single compositions as well as mixtures of gases with specific component ratios. The materials of the invention while widely applicable to many different gases are ideally suited for the manipulation of reactive gases, and more specifically, to reactive gases that have unique generation, storage, and delivery characteristics. An exemplary gas is chlorine dioxide.

Chemical and Physical Properties

Chlorine dioxide is a very reactive gas. It can not be compressed and stored as other gases and therefore cannot be transported in standard containers used for other gases. As a result, it must be generated when needed at the site of application. While this gas has exceptional utility in many applications, the inability to store it limits wide spread use.

Chlorine dioxide is very soluble in water and aqueous solutions and has been determined to be stable in concentrations of approximately 10 grams per Liter. Solubility is a function of temperature, pressure, and chemical composition of the liquid. Unlike carbon dioxide or chlorine gas, chlorine dioxide does not ionize in solution, and remains a true gas. Concentrated solutions of chlorine dioxide are pale yellow to brown in color and have an odor similar to chlorine. Gases such as chlorine, carbon dioxide, sulfur dioxide, and nitrogen containing gases also have significant solubility in solvents such as water.

Industrial Applicability:

Many laboratory studies have indicated that chlorine dioxide is an exceptional biocide and highly efficacious at killing bacteria, fungi, molds, algae, protozoa, viruses and cysts. It is excellent in treating biofilms. Chlorine dioxide is useful as a sterilization gas at high concentrations. It is approved by the USEPA, FDA, and USDA for many uses including sterilizing manufacturing and laboratory equipment, bleaching pulp, paper, and textiles, washing fruit and vegetables, disinfecting flume water, disinfecting meat and poultry, disinfecting food processing equipment, sanitizing water, controlling odors in hospitals, petroleum industries, and animal feedlots and rendering operations, treating medical waste, treating municipal water, anthrax decontamination, and cleaning of electronic circuit boards. The gas has been used to treat skin conditions, and wounds. Tissue inflammation in some cases may be treated. Chlorine dioxide has significant benefits in the treatment of recreational waters such as in pool and spa water. New applications are being developed rapidly as this strong oxidizer is recognized as being a much safer and more selective reactant than chlorine. Likewise, carbon dioxide, sulfur dioxide, and chlorine dioxide as well as inert gases have significant utility in controlling chemical and biological contamination in liquids, at solid interfaces, and in the local atmosphere around packaged articles.

Although chlorine dioxide contains chlorine, its reaction chemistry is predominantly through oxidation and not chlorination. This characteristic is highly beneficial as chlorinated reaction byproducts are undesirable in many applications including drinking water treatment. Additionally, chlorine dioxide is an efficient and rapid oxidizer of dissolved iron and manganese. Chlorine dioxide is very reactive towards phenols and sulfur containing molecules and thus is an efficacious odor control agent and decolorizing agent. Unlike the hypochlorite-hypochlorous acid system, chlorine dioxide is very effective over a broad solution pH range.

Generation of Chlorine Dioxide:

Site generation of chlorine dioxide has always been required since the gas is unstable in concentrated gaseous and aqueous solutions. Chlorine dioxide can be generated from both solid and solution phase reactions. Widely practiced reactions for preparing batches of chlorine dioxide include acidifying solutions of metal chlorite, introduction of a strong oxidizing agent such as hypochlorite into solutions of chlorite, or direct electrochemical oxidation of chlorite. Metal chlorate solutions may also be utilized in combination with chemical and electrochemical reduction reactions.

Preparation of Materials of the Invention:

The materials of the invention are prepared using absorbent and adsorbent materials combined with reactive gas precursor reagents, and liquids in which one or all gas related components exhibit solubility. Examples of reactive gases which are applicable to the invention include chlorine dioxide, carbon dioxide sulfur dioxide, hydrogen sulfide, ammonia, chlorine gas, dichlorine monoxide, hydrocyanic acid, nitrogen dioxide, nitrogen oxide, hydrogen, nitrogen, and oxygen. The materials of the invention may also contain soluble and suspended chemical and biological components in addition to the gas precursor reagents and the resultant gases. Additionally, multiple gas species may be simultaneously carried by the materials of the invention. In all cases, the materials of the invention are used to deliver reactive agents to a surface or fluid.

The example gases described can be prepared from simple and complex salts. In preparing the materials of the invention, the gas precursor reagents can be utilized in dry powder form, dissolved in a solvent, or when applicable, in a gaseous state. The liquids incorporated into the materials may be present prior to or during, or after gas generation. Gases may also be directly loaded into particles and fibers containing solutions thorough exposure to the gas, which is generated by external means. Detailed descriptions of suitable gas precursor reagents and methods for preparing examples of the reactive gases of the invention are provided herein.

Chlorine dioxide can be generated from solutions that contain the anion chlorite and an associated counter ion. Suitable chlorite sources include, alkali metal chlorites, such as sodium, lithium, and potassium chlorites, alkaline earth chlorites such as calcium and magnesium chlorite, chlorite salts of transition metals, chlorite salts of primary, secondary, and tertiary amines including ammonium chlorite, trialkylammonium chlorite and quaternary ammonium chlorite. Those skilled in the art will recognize that other chlorite salts are possible and the final application of the material will determine the optimum precursor species. Exemplary chlorite salts are those based on alkali metals.

Chlorine dioxide may also be generated using chlorate anions and an associated counter ion. Suitable chlorate sources include, alkali metal chlorates, such as sodium, lithium, and potassium chlorates, alkaline earth chlorates such as calcium and magnesium chlorate, chlorate salts of transition metals, chlorate salts of primary, secondary, and tertiary amines including ammonium chlorate, trialkylammonium chlorate and quaternary ammonium chlorate. Those skilled in the art will recognize that other chlorate salts are possible and the final application of the material will determine the optimum precursor species. Exemplary chlorate salts are those based on alkali metals.

Carbon dioxide gas is generated from solutions that contain the anions carbonate and bicarbonate and an associated counter ion. Suitable salts of these anions include alkali metal bicarbonates including sodium bicarbonate, potassium bicarbonate, and lithium bicarbonate, alkaline earth metal bicarbonates and carbonates, including calcium bicarbonate and calcium carbonate and magnesium bicarbonate and magnesium carbonate, bicarbonates and carbonates of primary secondary, tertiary and quaternary amines such as ammonium bicarbonate. A wide range of transition metal bicarbonates and carbonates may be used. Those skilled in the art will recognize that carbonate and bicarbonate are anions whose concentrations are also controlled in solution by adjustment of solution pH. Those skilled in the art will also recognize that many cationic polymer functionalities can provide the anions. Exemplary anions for generating carbon dioxide are the alkali metal bicarbonates.

Sulfur containing gases, such as sulfur dioxide and hydrogen sulfide can be generated from solutions that contain the anions sulfite, bisulfite and sulfide and an associated counter ion. Suitable sulfite and bisulfite salts include alkali metals salts of bisulfite and sulfite including sodium, potassium, and lithium, alkali earth metal bisulfites and sulfites, such as calcium and magnesium bisulfite and sulfite, and transition metal bisulfites and sulfites. Charged primary, secondary, tertiary, and quaternary amines of sulfites and bisulfites can be used. Suitable sulfide salts include alkali metals salts of sulfide including sodium, potassium, and lithium, alkali earth metal sulfides such as calcium and magnesium sulfides, and transition metal sulfides. Charged primary, secondary, tertiary, and quaternary amines of sulfides can be used.

Those skilled in the art will also recognize that many cationic polymers can provide the anions. Those skilled in the art will recognize that sulfite, bisulfite, and sulfide are anions whose concentrations are also controlled in solution by adjustment of solution pH. Those skilled in the art will also recognize that many cationic polymer functionalities can provide the anions. Exemplary salts for generating sulfur containing gases such as sulfur dioxide and hydrogen sulfide are the alkali metal sulfites, bisulfites, and sulfides.

Nitrogen containing gases including nitrogen, nitrogen dioxide, and nitrogen oxide can be generated from solutions that contain the anions nitrate and nitrite and an associated counter ion. Suitable salts of these anions include alkali metal nitrites and nitrates including sodium, potassium, lithium nitrite and nitrate, alkaline earth metal nitrites and nitrates, including calcium nitrite and nitrate and magnesium nitrite and nitrate and nitrites and nitrates of primary secondary, tertiary and quaternary amines such as ammonium nitrite and ammonium nitrate. A wide range of transition metal nitrites and nitrates may be used. Those skilled in the art will recognize that nitrite and nitrate are anions whose concentrations are also controlled in solution by adjustment of oxidation reduction potentials. Those skilled in the art will also recognize that many cationic polymer functionalities can provide the anions. Exemplary salts for generating nitrogen gases are the alkali metal nitrites.

Chlorine containing gases including chlorine and chlorine monoxide can be generated from solutions that contain the anion hypochlorite and an associated counter ion. Suitable salts of this anion include alkali metal hypochlorites including sodium, potassium, and lithium hypochlorite, alkaline earth metal hypochlorites, including calcium and magnesium hypochlorite and hypochlorites of primary secondary, tertiary and quaternary amines. A wide range of transition metal bicarbonates and carbonates may be used. Those skilled in the art will recognize that hypochlorite anion concentrations are also controlled in solution by adjustment of solution pH. Those skilled in the art will also recognize that many cationic polymer functionalities can provide the anions. Stabilized hypochlorite/hypochlorous acid solutions may also be used. Exemplary salts for generating chlorine containing gases are the alkali metal hypochlorites.

Cyanide gas can be generated from solutions that contain the cyanide anion and a counter ion. Suitable salts of this anion include alkali metal cyanides including sodium, potassium, and lithium cyanide, alkaline earth metal cyanides, including calcium and magnesium cyanide and cyanides of primary secondary, tertiary and quaternary amines. A wide range of transition metal cyanides may be used. Those skilled in the art will recognize that cyanide anion concentrations are also controlled in solution by adjustment of solution pH. Those skilled in the art will also recognize that many cationic polymer functionalities can provide the anions. Exemplary salts for generating cyanide gases are the alkali metal cyanides.

Oxygen gas can be generated from solutions that contain peroxides or compounds generating peroxides, including organic or inorganic peroxides, peracids, percarbonates, or persalts. Preferred agents include hydrogen peroxide, peracetic acid, and monoperoxysulfate. A number of peroxides, peracids, and persalts have been disclosed by Fong in U.S. Pat. No. 4,964,870. This disclosure is incorporated in its entirety by reference.

Acids Used to Generate Gases:

Many exemplary reactive gases of the invention including chlorine dioxide, carbon dioxide, and sulfur and nitrogen containing gases can be generated by exposure of the gas precursor anions to acidic liquids, gases, or a combination thereof. Acids and more particular hydronium ions or protons can be provided by a wide range of chemical agents and through the presence of degradable chemical agents. Acid generating agents include water, protonated solvents such as alcohols, organic acids and inorganic acids. Acid provided by organic agents include, carboxylic acids, examples include acetic acids and naturally occurring acids. Both tartaric and citric acids are excellent agents for generating the reactive gases. Acid provided by organic agents also include, esters, anhydrides, acyl halides, carboxylates of polyhydroxyalcohols, degradable polyesters including polylactic acid, polyglycolic acid, polyacrylic acid and copolymers, polyacrylamide and copolymers, poly-beta-hydroxybutyrate, polylactone, anhydride or phosphate esters blended with or grafted to polypropylene, polyethylene, or polystyrene.

Acid anhydrides include organic acid anhydrides, mixed organic ahydrides, homopolymers of organic acid anhydrides, mixed inorganic acid anhydrides, copolymers of organic acid anhydrides, and mixed organic acid anhydrides containing conjugation. Exemplary anhydrides include polymers containing anhydrides including, maleic anhydride, methacrylic anhydride, acetic anhydride, propionic anhydride, succininc anhydride, vinyl, styrene, or alkene containing polymers, as well as polymers including esters of lactic and glycolic acid monomers.

Many polymers, copolymers, and grafted polymers are capable of providing hydronium ions and protons for gas generation. Exemplary polymers include xanthum gum, polyvinylpyrrooidone, polyvinylalcohols, polyanhydrides, polyacrylamides, lactic acid based polymers, glycolic polymers, hydroxyl acids, and mixtures thereof. Those experienced in the art will recognize that the amount of polymer-sourced acid provided to a system is based upon polymer molecular weight, amount of polymer present, and solubility characteristics of the different chemical species.

Inorganic chemical species and chemical agents that contain halides, phosphorus, silicon, sulfur and boron are excellent sources of acid for generating gases of this invention. Mineral acids, including hydrofluoric, hydrochloric, hydrosulfuric, hydrobromic, hydroiodic, phosphoric, boric, and silic acid are exemplary. The materials of the invention can use a wide concentration range of these acids including commercially available concentrates. Additional inorganic acid providing chemical species include, phosphate esters, trialkylsilylphosphate, sulfonic acid esters, sulfonic acid chlorides, phosphosilicates, phosphosilicate anhydrides, phosphosiloxanes, tetraalkyl ammonium phosphates, monobasic phosphates based on alkali metals, polymetaphosphates based upon alkali metals, borophosphates, aluminophosphates, silicophosphates, polyphosphates such as sodium and potassium tripolyphosphate, and mixed tripolyphosphates. Particulate metals and metal oxides can provide acid in order to generate gases of the invention. Oxides based upon aluminum, iron, silicon, and transition metals are applicable. Suitable salts for generating acid include metal salts such as iron chloride, iron sulfate, zinc sulfate, zinc chloride, cobalt sulfate, cobalt chloride, manganese sulfate, manganese chloride, copper sulfate, copper chloride, and magnesium sulfate.

Bases Used to Inhibit Gas Formation:

Materials of the invention can use chemical agents to control, stabilize, or inhibit the generation of gases of the invention. These methods are well understood in the field. As example, technical grade sodium chlorite is formulated with approximately twenty percent carbonate and sulfate species. The formulation yields a strongly alkaline pH upon dissolution. Alkaline pH solutions containing chlorite minimize the generation of chlorine dioxide gas. Bases and chemical species capable of reacting with acid compounds through neutralization of hydronium ions or accepting protons serve as a mechanism for inhibiting the reaction of acids with the anion precursors to the gases of the invention. Exemplary chemical agents include caustics prepared with alkali metals including sodium, potassium, and lithium hydroxides, as well as alkaline earth hydroxides such as calcium and magnesium hydroxides. Amines such as ammonia and ammonium hydroxide have acid neutralization capacity as do bicarbonates, carbonates, phosphates, sulfates, borates, and the salts of organic weak acids such as acetates. Those skilled in the art will recognize the wide range of acid neutralization chemical which are available.

Reduction Agents Used to Inhibit Gas Formation

Chlorine dioxide gas can be generated through oxidation with chemical agents or through electrochemical reaction. Exemplary agents include chlorine based oxidizers. Suitable chlorine containing species include chlorine gas, hypochlorites based on alkali salts and alkali earth salts. Stabilized chlorine species using cyanuric acid are also useful oxidizing agents. Compounds that neutralize these chlorine based oxidizing agents inhibit the generation of chlorine dioxide gas. Exemplary neutralizing agents include bisulfites, thiosulfates, reduced metals, and activated carbons. Reducing agents may also be used to increase the temperature of the system which allows further control over gas concentrations and delivery parameters. In some cases, portions of the oxidizing agent generated is used or sacrificed to increase system temperature.

Adsorption and Absorption Materials of the Invention:

The absorbent particles and fibers of the invention can be obtained from a variety of natural and synthetic sources and can be used to control the delivery of the reactive treatment agents. These particles and fibers can be entirely composed of organic materials, inorganic materials, or combinations thereof. Further, the absorbent materials may be homogeneous or heterogeneous in distribution of the different synthetic, natural, organic, or inorganic components. Those familiar with the technology and art of absorbency also understand that adsorption occurs at the surface of these materials and that both molecular scale and bulk scale solvent and solute interactions can occur in simultaneous and continuous fashion. Additionally, those experienced in the art of preparing absorbent materials understand that nonwoven, woven, and combinations thereof, the treatment of fiber through chemical, physical and combinations thereof methods, as well as wrapping and layering sheets of similar and differing materials have considerable impact on material functional properties.

Absorbent materials suitable for the invention include sponges, foams, and absorbent minerals and polymers. These materials may be in the form of particles, fibers, or combinations thereof. Foams and sponge materials can hold and contain liquids in widely varying amounts based upon preparation methods. Sponge materials can be naturally occurring or synthetic. Applicable materials include polyethers, polyesters, polyurethanes, celluloses, polyethylenes, polyvinylalcohols, corks, and butyl rubbers and copolymers of the different species. Pore and cell type, open or closed, and size can be modified to change absorption properties. Foam materials can be further treated to be fire retardant, flexible, or semi rigid. Manufacturing methods such as reticulation also effect absorbency. Additionally, woven and non-woven materials have the capacity to adsorb and absorb fluids. The type of fluids and capacity of uptake are dependent upon fiber types, manufacturing methods and surface treatment. Foams, sponges, and fiber absorbents carry chemical compatibility characteristics related to their composition and method of manufacture. Those skilled in the art will recognize and understand the chemical compatibility requirements of the different materials.

Exemplary materials for holding liquid reagents include those materials such as super-absorbent polymers and absorbent minerals that do not release liquids upon changes in pressure and temperature. The capacity to tightly hold the liquids containing reactive precursor reagents required for reactive gas generation and subsequently liquids that contain high concentrations of reactive gases increase the safety in generating, storing, and applying reactive gases to a wide range of applications.

Exemplary materials of the invention are stable in the presence of highly caustic solutions of metal chlorites, and chlorate solutions, in concentrated acids, and in the presence of high concentrations of reactive gases including chlorine dioxide, carbon dioxide, and gases containing nitrogen, oxygen, and sulfur. As example, caustic solutions of sodium chlorite are known to be stable for long periods of time. Absorbent articles that are stable with both anions and caustic are suitable materials. Similarly, absorbent articles that are stable with both cations and acids are suitable materials. These materials each containing a different reactive species may be combined to yield the desired gas. After generation of the gas, the gas is soluble in the liquid contained by the materials. Materials which are stable to chlorine dioxide, carbon dioxide, and sulfur and nitrogen gases are well known.

Exemplary inorganic materials capable or retaining liquids include smectic type minerals. Inorganic sources of liquid carrying and absorbent particles include aluminosilicates, smectic or montmorillinite clays, and preferred materials including, bentonite, attipulgite, and expanded silica.

Preferred and applicable absorbent material for absorption of fluids of the invention may be generated from a range of synthetic and natural polymer materials. The class of materials known as "superabsorbents" is particularly suitable in this regard. Superabsorbents are natural, synthetic, or mixed polymers that are not fully cross-linked. They may be classified as polyelectrolyte or nonpolyelectrolyte types as well covalent, ionic, or physical gelling materials. These materials have the capacity to absorb many times their own volume in fluid. Examples of synthetic materials include polyacrylic acids, polyacrylamides, poly-alcohols, polyamines, and polyethylene oxides. The composite superabsorbent material may also be selected from derivatives of polyacrylic acids, polyacrylamides, poly-alcohols, polyamines, polyethylene oxides, cellulose, chitins, gelatins. starch, polyvinyl alcohols and polyacrylic acid, polyacrylonitrile, carboxymethyl cellulose, alginic acids, carrageenans isolated from seaweeds, polysaccharides, pectins, xanthans, poly-(diallyldimethylammonium chloride), poly-vinylpyridine, poly-vinylbenzyltrimethyl ammonium salts, polyvinylacetates, polylactic acids, or combinations thereof. The composite material may also comprises a material selected from resins obtained by polymerizing derivatives of acrylic acid or resins obtained by polymerizing derivatives of acrylamide.

Biodegradable materials that are suitable include cellulose derivatives, chitins, and gelatins. Additionally mixtures of synthetic polymer and natural polymers either as distinct chains or in copolymers may be used to generate these absorbent materials. Examples include starch polyacrylic acid, polyvinyl alcohols and polyacrylic acid, starch and polyacrylonitrile, carboxymethyl cellulose, alginic acids carrageenans isolated from seaweeds, polysaccharides, pectins, xanthans, poly(diallyldimethylammonium chloride), polyvinylpyridine, polyvinylbenzyltrimethylammonium salts, cellulose, alginic acids, carrageenans isolated from seaweeds, polysaccharides, pectins, xanthans, starch, or combinations thereof, polyethyleneglycol, a polylactic acid, a polyvinylalcohol, a co-polylactideglycolide, cellulose, alginic acids, carrageenans isolated from seaweeds, polysaccharides, pectins, xanthans, and starch.

As those experienced in the art will understand the process of cross-linking polymer chains derived from either any source or combinations of sources, are variable and will affect the magnitude of fluid absorption, and the types of fluids that may be absorbed. Additionally those experienced in the art will understand that molecular characteristics such as polymer chain composition, functional group position and distribution as well as polymer molecular weight and distribution will effect performance, and will know how to modify these parameters to vary the properties of the resulting composite consistent with the basic tenets of the invention. Further those experienced in the art will understand that the volume capacity of a material is also subject to the type and composition of the fluid in which the material is exposed.

Addition of Soluble Salts and Other Soluble Compounds

Exemplary materials of the invention provide control of liquids and gas containing liquids and also have the capacity to hold (adsorb/absorb) significant volumes of liquids including water and other polar solvents. The use of different liquid compositions controls gas generation, storage, and delivery characteristics. Likewise exemplary materials of the invention exist for containing (absorb/adsorb) significant volumes of nonpolar solvents. The use of different nonpolar liquid compositions controls gas generation, storage, and delivery characteristics. As a result, soluble agents can be retained by the particles and fibers of the invention in addition to the gas precursor reagents and gases. Exemplary agents include soluble metals, chelating agents, metal ligands, biocides, amines such as quaternary amines, organic acids such as fatty acid, micelles, and emulsions. Polar solvents such as alcohols, ethanolamines, and polar organic solvents with solubility in water are applicable and allow solubilization of active chemical and biological species. Many biological components including DNA, RNA, proteins, peptides, and associated molecules are soluble in water and polar solvents. Exemplary biological agents include, enzymes, protein fragments, and emulsions or micelles that contain these agents. Those skilled in the art will recognize that combinations of certain soluble, suspended, and reactive agents are not compatible and will neutralize or generate undesirable or unwanted chemical species. Additional exemplary agents include alcohols, fragrances, odor neutralizing agents, odor masking agents, disinfecting agents, preservatives, biocides, bacteriostats, fungistats, osmostic regulators, sequestering agents, chelating agents, and binders pesticides, insecticides, herbicides, pheromones, and animal attractants, cleaning solutions, fatty acids, soaps.

Addition of Solution Viscosity Modifiers

Materials of the invention have the unique capacity to contain liquids with widely varying viscosities. Liquid viscosity can impact the generation, storage, and delivery of the reactive treatment gases. Liquids suitable for the invention can be modified with food, medical, or industrial grade viscosity agents including magnesium containing minerals, betaines, celluloses, methylcelluloses, xanthum gums, acrylates, acrylamides, polyalcohols, polyethylenglycols, polyesters, and naturally occurring and synthetically produced polymers, copolymers, and grafted polymers. Those skilled in the art will understand the importance of molecular weight and solubility characteristics of these compounds when used as solution viscosity modifiers.

Addition of Suspended Particulate Material

Liquids contained by the materials of the invention can carry suspended particulate matter including nanoparticles consisting of metals, alloys, metal oxides, and a combination thereof, and these suspended agents can impact the generation, storage, and delivery of reactive treatment agents. Nanoparticles can contain surface reactive chemicals such as metal ions and organic functionalities. Preferred and applicable materials include naturally occurring, synthetic, and recycled materials. Suitable materials include insoluble minerals and metals. Synthetic and natural fibers, including strings, yarns and textiles including, cotton, wool, polypropylene, rayon, polyester, nylon, acrylic are also applicable.

Addition of Non-Solvent Carrying Particles

Particles and fibers with the capacity to uptake and contain liquids and gas precursor reagents can be mixed and combined in simple or complex formulations with particles, fibers, or a combination thereof, that have limited fluid uptake or solution control characteristics. These materials can have an impact on the generation, storage, and delivery of reactive treatment agents. Exemplary materials include desiccants, amorphous silicates, zeolites, metal oxides and hydroxides, carbonates, phosphates, and reduced metals. Those skilled in the art will recognize that liquid transfer between particles types can occur, and this transfer can modify the surface and pore properties of each particle type. Those skilled in the art will also recognize that materials that carry liquids containing reactive agents may be incompatible with certain additional particle types. As example materials of the invention that contain the gas carbon dioxide will have significant gas concentration loses when mixed with caustic particles such as carbonates and magnesium oxides. Preferred and applicable materials include naturally occurring, synthetic, and recycled materials. Suitable materials include aqueous insoluble metal salts.

Synthetic and natural fibers, including strings, yarns and textiles including, cotton, wool, polypropylene, rayon, polyester, nylon, acrylic are also exemplary. Ion exchange material is a preferred material and includes resins selected from functionalized styrenes, vinylchlorides, divinyl benzenes, methacrylates, acrylates, or mixtures, copolymers, and blends thereof. Natural and synthetic zeolites such as clinoptilolite and glauconate are preferred.

Catalytic materials involving metals and enzymes are quite common and these are applicable in all known forms. Those experienced in the art will recognize that the deposition of molecules containing active sites that include metals and atoms and nanocomposites of metals and semimetals on the surface of support materials are immediately applicable.

Those experienced in the art will also understand that the particulate and fiber materials of the invention may be surface modified with a range of compounds and through different binding methods. Preferred surface modifications yield cationic surface functionalities. Examples of preferred surface modification chemicals include chemical agents selected from 3-acryloxypropylotrichlorosilane, 3-acrlyoxypropylotrimethocysilane, Allyltrichlorosilane, allyltrimethoxysilane, allyltriethoxysilane, 3-bromopropylotrichlorosilane, 3-bromopropyl-trimethoxysilane, (p-chloromethyl)phenyltrichlorosilane), (p-chloromethyl)phenyltrimethoxy silane, 1-trimethoxysilyl-2-2(p,m-chloromethyl)-phenylethane, chloromethyltrichlorosilane, chloromethyltriethoxysilane, 2-chloroethyltriethoxysilane, 3-chloropropyltrichlorosilane, 3-chloropropyl-trimethoxysilane, 3-glycidoxypropyltrimethoxysilane, 3-iodopropyl trimethoxy silane, 3-isocyanatopropyltriethoxysilane, 2-(diphenylphosphino) ethyltriethoxysilane, vinyltriacetoxysilane, vinyltrichlorosilane, vinyltriethoxysilane, vinyltrimethoxysilane, 3-mercaptopropyltrimethoxysilane, 3-mercaptopropyltriethoxysilane, N-(triethoxysilylpropyl)urea, 3-aminopropyl-triethoxysilane, 3-aminopropyltrimethoxy silane, N-(2-aminoethyl)-3-aminopropyltrimethoxysilane, 2-(carbomethoxy)ethyltrichlorosilane, N-[(3-trimethoxysilyl)-propyl] ethylenediamine triacetic acid, trisodium salt, 3-cyanopropyltrichlorosilane, 3-cyanopropyltriethoxysilane, 2-(4-chlorosulfonylphenyl)ethyltrichlorosilane, 2-(4-chlorosulfonylphenyl) ethyltrimethoxysilane, 2-(trimethoxysilyl)ethyl-2-pyridine, N-(3-trimethoxysilylpropyl)pyrrole, N-octadecyldimethyl-1(3-trimethoxysilyl) propyl]ammonium chloride, N-trimethoxysilylpropyl-n,n,n-trimethyl ammoniym chloride, 3-(trimethoxysilyl)propyldimethyloctadecylammonium chloride silane quaternary amine, chloropropyl trihydroxy silane, polyamines, polyamides, polyalcohols, polysaacharides, polyacrylamides, polyacrylates, humic acids, peptides, proteins, polorganozirconates, polyorganoaluminates, polysiloxanes, polysilanes, polysilazanes, polycarbosilanes, polyborosilanes, zirconium dimethacrulate, zirconium tetramethacrylate, zirconium 2-ethylhexanoate, aluminum butoxides, aluminum diisopropoxide ethylacetoacetate, tetramethyldisiloxanes and derivatives thereof, tristrimethylsilylphosphate and tristrimethylsiloxyboron, polyamines such as poly(DADMAC), poly-DADM, polyamine-poly(DADMAC) blends, polyquartenary amines, inorganic-polyamine blends, and inorganic poly(DADMAC) blends, cationic starch, cationic poly-methylmethacrylates, copolymers of vinylimidazolium methochloride and vinylpyrrolidone, quarternized vinylpyrrolidone/dimethylaminoethyl-methacrylate copolymer, polyethyleneimine, or combinations thereof.

Additionally, surface binding methods that provide the capacity of immobilizing biological material, proteins, peptides, antibodies, and pharmaceutical agents are preferred means of modifying the surfaces of all solid materials. Those experienced in the art will recognize that numerous procedures exist for generating stable surface coatings of these materials. Furthermore the ability to immobilize genetic information as well as proteins and peptides facilitates the use of the materials of the invention in sensing and sensor development during gas generation, while containing reactive gases, or after the gas has been utilized.

Particulate and fiber material may be in the form of particles ranging in size from 0.05 microns through 100 millimeters, fibers with diameters of 0.05 microns through 100 millimeters, or combinations thereof. Materials that do not have significant fluid uptake properties may have similar sizes. Homogeneous and heterogeneous particle and fiber mixtures can be widely varying. Additionally, those experienced in the art will understand that particles and fiber size distributions affect many treatment parameters as well as safety. Further, particles and fibers that interact with solvents can have a widely varying particles size due to fluid uptake.

Polycarbonate:

A preferred material for use in the invention is polycarbonate. It has been observed that polycarbonate has a significant capacity for storing and releasing chlorine dioxide. Polycarbonate can contain concentrations of chlorine dioxide great enough to yield a colored material. When exposed to solutions of high concentrations of chlorine dioxide yellow colored polycarbonate objects are obtained. The gas contained by the carbonate can be released over time and is available for the applications described herein. Flushing of the gas and solvent from polycarbonate can be observed by the loss of color. This preferred material is used commonly in eyewear, the medical and surgical field, and to produce objects with high impact resistance. The unique interaction of polycarbonate with chlorine dioxide facilitates the design and application of high impact objects that possess the capacity to control chemical and biological contaminants at their surface.

DETAILED DESCRIPTION OF THE FIGURES

Figure 1:
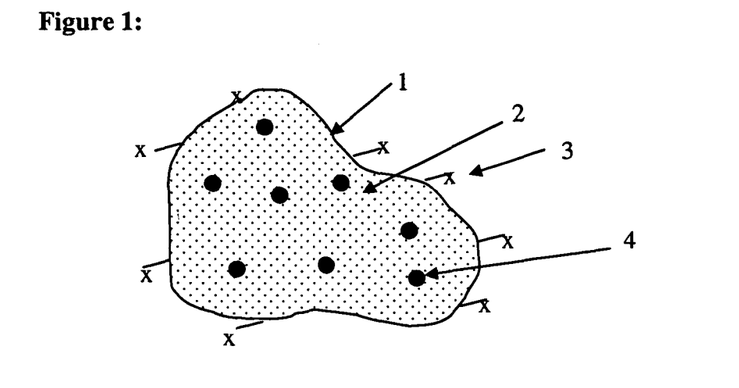
FIG. 1 illustrates one embodiment of the invention, a polymer particle with surface reactive groups which contains an aqueous solution of chlorite metal salt and chlorine dioxide.

FIG. 1 illustrates one embodiment of the invention, a polymer particle, (1), containing and aqueous solution of the precursor reagent sodium chlorite, (2), reactive particle surface agents, (3), and reactive gas chlorine dioxide, (4).

Figure 2:
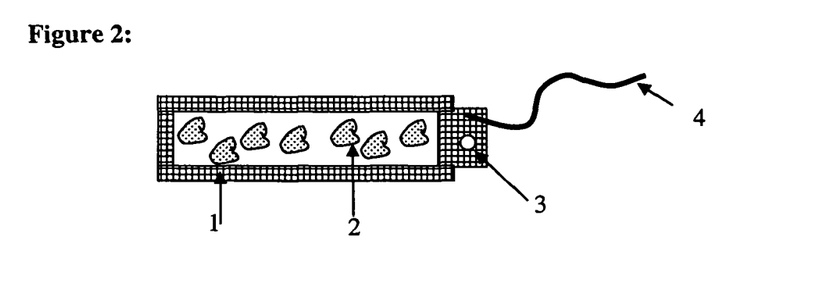
FIG. 2 illustrates one embodiment of the invention, a sachet containing particles of the invention. This sachet can be used for direct release of a gas to an atmosphere or for preparation of a secondary liquid solution.

FIG. 2 illustrates one embodiment of the invention, where particles containing the reactive gas chlorine dioxide, (1), are a contained in a gas porous sachet composed of a transparent gas permeable membrane, (2). The sachet, (2), contains an optional hole, (3), for mounting the sachet, (2), and an optional string, (4), for manipulating the sachet, (2).

Figure 3:
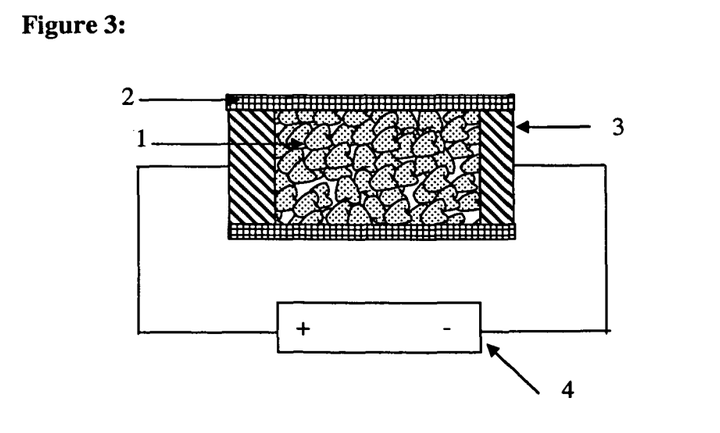
FIG. 3 illustrates one embodiment of the invention, a small container composed of a gas permeable material, a transparent window for visualizing color, and containing particles of the invention containing a metal chlorite solution. This device allows release of electrochemically generated chlorine dioxide, when connected to a power supply.

FIG. 3 illustrates one embodiment of the invention, a small container composed of a gas permeable transparent material, (2), containing polymer particles containing a solution of sodium chlorite, gas precursor, (1). This container is fitted with electrodes, (3), which are connected to a power supply, (4). This device allows release of electrochemically generated chlorine dioxide, without bulk exchange of liquid to the surrounding atmosphere or liquid while at the same time allowing the color of the particles to be viewed for determining the amount of remaining useful lifetime.

Advantages of the Materials of the Invention:

There are many methods of preparing and practicing the invention using the combination of gas precursor reagents, liquids with gas solubility (storage capacity), and absorbent articles for control and manipulation of all components. In general, practice of the invention involves the combination of absorbent/adsorbent particles, fibers or a combination thereof, which have limited reaction with the precursor reagents, reactive gas precursor reagents, and a liquid in which the gas precursor reagents, the generated gas, or a combination thereof have solubility. Absorbent and adsorbent materials utilized in this invention can include natural and synthetic polymers in particle, fiber or sheet form, natural and synthetic materials such as sponges, and natural and synthetic minerals which have substantial liquid carrying capacity. Many of these materials can swell or expand upon liquid uptake and provide strong liquid retention even under pressure. In strong contrast to prior art the absorbent materials are utilized in a manner which allows rapid mixing and reaction of gas precursor reagents, controlled distribution and delivery of gases, and a reservoir or depot for both reagents and gases. This depot of reagents and reactive gases in particle and fiber form provides great safety and convenience in utility and ultimately in application of high concentrations of the reactive gases.

The particles and fibers of the invention can be combined with the liquids and the reactive gas precursor agents in several simple methods. In general, particles and fibers can be prepared with the individual precursor reagents of the gas generation reaction. Specifically, different particles and fibers are used to contain a single gas precursor reagent. When separate particle types are mixed the precursor reagents contained react through bulk fluid transfer and diffusion, ultimately yielding particles with similar composition, and containing the generated gas to the capacity of the liquid. Gas in excess of the solubility limit, as determined by chemical and physical parameters of the liquid, will escape to the surrounding solution or atmosphere.

Alternatively, all components; particles, fibers, or combinations thereof, and precursor reagents may be combined into a single composite in dry form. Upon exposure to a liquid the gas precursor reagents react, gas is generated, and the liquids and gases are contained by the particles, fibers, or combinations thereof. Additional alternative methods include, introducing one of the precursor reagents in dry form or gaseous form to the components, particles, fibers, or combinations thereof, which contain a solution of the precursor reagents. Upon exposure to the liquid containing particles or fibers the dry or gaseous reagents dissolve and react, again yielding gas and liquids which are absorbed/adsorbed by the particles and/or fibers.

Alternatively, the particles and fibers of the invention which carry dissolved precursor reagents may be directly reacted in electrochemical systems. In these systems, electrodes and a power source are used to generate the gas. The gas is dissolved in the liquids which are contained by the particles or fibers. Further, the particles can obtain precursor reagents through direct chemical or electrochemical reaction before gas generation reactions are initiated. As example, acidic liquids can be generated in the particles and fibers through electrochemical reaction of compounds such as water which are contained in the particles or fibers. Similarly, chloride ion can be electrochemically oxidized to free chlorine, which reacts quickly when chlorite is present or introduced into solution.

Many of the preferred synthetic polymers and minerals are those that are stable in concentrated acids and bases, and which strongly absorb and retain solutions of these chemicals. Such materials do not release the absorbed liquid easily by applying external pressure. The liquids contained in these materials serve as both a storage depot for the molecules and ions that react to form the reactive gases, as well as the generated gas. Further these particle or fiber vessels may also contain additional chemicals which are useful in combination with the generated gas and precursor reagents. Examples include, pH modifiers, ion controlling agents, colored indicators, fragrances, and surfactants. Furthermore, the particles and fibers of the invention can be mixed with non-liquid containing particles and fibers for preparation of unique treatment materials. Even further the materials of the invention can be combined with and contained in membrane, selective and defined porosity materials for controlling release of the reactive gas to the surroundings and to control exposure of the materials of the invention to components in the surroundings.

The invention described herein provides a method of conveniently and safely mixing hazardous solutions which contain chlorine, sulfur, carbon, oxygen, and nitrogen compounds, caustics, acids, and a wide range of chemical reagents that yield gases and useful chemical agents. The invention provides a convenient method of storing reactive gases and subsequently delivering the reactive gases to many applications. The materials and methods of the invention are environmentally friendly in that they can readily utilize natural and synthetic materials which are biodegradable. Additionally, absorbent materials exist for hydrophobic and non-polar liquids and these materials in combinations with their associated liquids are capable of acting as storage depots for chemical reagents and the reaction products of those chemical reactions, including gases. It is possible to extract gases between particle types and solvent types.

The materials of the invention have many unique properties. The materials of the invention that contain chlorine dioxide can be exceptional biocides and highly efficacious at killing bacteria, fungi, molds, algae, protozoa, viruses and cysts. Chlorine dioxide is excellent in treating biofilms. Chlorine dioxide is useful as a sterilization gas at high concentrations. It is approved by the USEPA, FDA, and USDA for many uses including sterilizing manufacturing and laboratory equipment, bleaching pulp, paper, and textiles, washing fruit and vegetables, disinfecting flume water, disinfecting meat and poultry, disinfecting food processing equipment, sanitizing water, controlling odors in hospitals, petroleum industries, and animal feedlots and rendering operations, treating medical waste, treating municipal water, anthrax decontamination, and cleaning of electronic circuit boards. The gas has been used to treat skin conditions, and wounds. Tissue inflammation in some cases may be treated.

Chlorine dioxide is has significant benefits in the treatment of recreational waters such as in pool and spa water. New applications are being developed rapidly as this strong oxidizer is recognized as being a much safer and more selective reactant than chlorine. Likewise, carbon dioxide, sulfur dioxide, and chlorine dioxide as well as inert gases have significant utility in controlling chemical and biological contamination in liquids, at solid interfaces, and in the local atmosphere around packaged articles.

A number of examples are described herein for the preparation, manipulation, and storage of the materials of the invention. The materials prepared are suitable for applications where the reactive gas is used to treat a surrounding atmosphere, transfer a reactive gas to a liquid, and to provide materials suitable for the direct cleaning of surfaces through incorporation in standard cleaning products such as wipes, towels, scrubbers, and handheld tools.

The materials and methods of the invention do not require the use of silicate, zeolite, desiccant, or common tablet preparation compounds to produce materials that are convenient to handle and apply, and to store the sensitive precursor reagents. The materials and methods of the invention do not require sophisticated drying or packaging technologies.

One of the many advantages of the invention described herein is the capacity to generate and transfer highly purified chlorine dioxide gas to an application without transfer of bulk reaction liquid which can contain unreacted precursor reagents, reagents present in excess, or contaminants or reaction byproducts that were initially present in the reaction solution or formed through undesirable reactions. Gas transfer can be completed through atmosphere contact or through the use membranes and porous materials. Another advantage includes the ability to treat a surface including, liquid sensitive surfaces such as circuit boards, electronic equipment and machinery with a high concentration of biocidal gases without the transfer of bulk liquid to the surface. The materials of the invention are ideal for preparing sachets containing biocidal gases which can be included with packaged items including food, medical equipment, military materiel, and artifacts.

Another advantage of the materials of the invention include the ability to simultaneously absorb and control liquid spills and wastes and neutralize, decontaminate, and sterilize components of the liquid. Likewise, materials of the invention can simultaneously absorb powders, through dissolution or simple uptake by the liquid held by the particles or fibers, and neutralize, decontaminate, and sterilize the components of the powder. This beneficial characteristic of the materials of the invention allow the materials to be used, in food processing for the containment of meat, poultry, and fish juices. As example, juice from meat poultry and seafood, collect at the bottom of trays used to package the items. Materials of the invention containing the precursors for chlorine dioxide allow simultaneous uptake of the acidic fluids, keeping the food dry, and generation of chlorine dioxide which prevents microbial growth in the fluid and the surface of the item.

Materials of the invention can be used to control and treat personal fluids found in hospitals and medical situations including, blood, urine, and tissue fluid. The materials of the invention allow simultaneous uptake and solidification (gelling) of these fluids while releasing a strong biocidal gas that diffuses through the container holding these materials. Treatment of these fluids in this manner significantly reduces the hazards associated with contagion transmission.

Materials of the invention can be used to control and treat unknown liquids and powders that are believed to contain biological and chemical agents intended to be used as a weapon or terrorizing agent. The chemicals associated with the neutralization and hydrolysis of chemical weapons are compatible with the materials of the invention, and include, acids, caustics, ethanolamine, and surfactants. The materials of the invention can simultaneously take up the unknown liquid or powder, neutralize it, and provide a safe disposal option.

The materials of the invention can be stored in many containers and packages using a wide range of materials, including polymers, glass, and foil coated materials. Exemplary materials include Teflon, tyvek, polycarbonate, and polyethylene. Porosity and headspace volume affect loss of gas from the particles. Another beneficial characteristic of the materials of the invention include the ability to minimize container headspace volume through the volume expansion of some particle types. In effect, a container is filled to capacity by proper ratio of liquid, particles, and precursor reagents.

The materials of the invention can be formulated with biodegradable materials thus minimizing impact on the environment after they are depleted. Gases such as chlorine dioxide are also soluble in nonaqueous liquids and thus may be extracted and used in other systems allowing the original materials to be recycled.

A variety of methods may be used to prepare the materials of the invention. The reactive gas chlorine dioxide is used to exemplify the materials, methods and utility of the invention. Specifically, the reactive gas chlorine dioxide is generated with solution phase, solid phase, and gas phase reactions in particles, composed of polymers and containing aqueous solutions. Additionally, chlorine dioxide gas, generated by external means, is loaded into aqueous solution containing polymer particles through direct exposure. Further chlorine dioxide gas is generated in particles by exposing particles containing chlorite to an electrode surface. Chlorine dioxide is transferred to a secondary solution by transfer of polymer particles containing the gas. It should be noted that the following exemplary descriptions are a small subset of the materials and applications that are possible with the art described herein.

EXAMPLES

Example 1

Generation of ClO2 Via Polymer/Tap-Water Contact

Sodium chlorite, technical grade, was dissolved in tap water and mixed with commercially available polyacrylic acid and polyacrylamide containing polymer particles. These polymer particles quickly absorb solutions of sodium chlorite. Slowly, over a period of time, a faint chlorine smell is detected from the container of particles and the individual particles obtain a faint green color. The particles containing chlorine dioxide are stable over a wide temperature range for many weeks. When exposed to the atmosphere the particles slowly return to their original clear form.

Example 2

Generation of ClO2 Via Mixing of Individual Precursor Particles

Sodium chlorite, technical grade, was dissolved in tap water and mixed with absorbent polyacrylic acid and polyacrylamide copolymer particles. The polymer particles absorbed the chlorite solution. Hydrochloric acid, 31%, was added to water and this solution mixed with polyacrylic acid and polyacrylamide copolymer particles. The polymer particles absorbed the acid solution. Subsequently, the two different particle types, sodium chlorite solution particles and the acid solution particles were mixed homogeneously. Over time, the particles turn different shades of yellow, and a strong chlorine smell can be detected from the container housing the particles. The solution precursor concentration contained by the two particle types directly affects the rate in which the particles generate chorine dioxide gas and obtained a yellow color.

Example 3

Generation of ClO2 Via Chlorite Pellet and Acid Solution Containing Particles

Sodium chlorite, technical grade, was compressed into a pellet using a small hand press. Hydrochloric acid, 31%, was added to water and the subsequent solution absorbed into polyacrylic acid and polyacrylamide copolymer particles. The pellet containing sodium chlorite was placed into contact with the acid solution containing particles. The polymer particles in direct contact with the sodium chlorite pellet immediately turned brown in color, while particles not in direct contact with the pellet slowly obtained various shades of yellow. After complete dissolution of the sodium chlorite pellet all particles obtained the same shade of yellow, indicating diffusion of the chlorine dioxide gas throughout the polymer particles.

Example 4

Generation of ClO2 Via Direct Acid Injection to Chlorite Particles

Sodium chlorite, technical grade, was mixed with polyacrylic acid and polyacrylamide copolymer particles and placed in a container. A hydrochloric acid solution was introduced directly on to the polymer particles containing the chlorite solution and the container sealed. The introduced acid solution was immediately absorbed by the particles and golden brown colored particles were generated. A strong chlorine smell can be observed from the container.

Introduction of several golden brown particles to a small volume of water, generated a bright yellow solution and the polymer particles became colorless. This solution was capable of rapidly removing the blue color from iodine soaked paper.

Example 5

Packaging of ClO2 Containing Particles of the Invention

The chlorine dioxide containing particles described in Examples 1-4 were vacuum packaged using a commercially available household food vacuum sealing equipment. All particle types and solution concentrations could be packaged. Particles containing high enough concentrations of chlorine dioxide to yield yellow colors were observed to be stable in these packages for many weeks.

Example 6

PACKAGING OF ClO2 Containing Particles with Tyvek Membrane Material

The chlorine dioxide containing particles described in Examples 1-4 were place in a sachet type containers prepared with tyvek membrane material and a nonporous polyethylene sheet. This sachet was subsequently vacuum packaged using commercially available household food sealing equipment. Particle color observed by eye through the non-tyvek material indicated no color change over many weeks. Exposure of the sachet to the atmosphere eventually yielded white and then clear particle forms.

Example 7

Generation of ClO2 Via Exposure to Acid Gas

Sodium chlorite solutions were prepared with tap water and absorbed into polyacrylic acid and polyacrylamide copolymer particles. The particles were exposed to acetic acid vapors, using vinegar as a source. The sodium chlorite polymer particles turned greenish yellow in color after exposure to the acetic acid fumes indicating that the polymer particles have the ability to absorb acid gases and that the chlorite present was available for the generation of chlorine dioxide gas. The polymer particles are stable and retain color in the acetic acid atmosphere for many months.

Example 8

Gas Phase Chlorine Reaction to Generation ClO2 in Particles

Sodium chlorite solutions were prepared with tap water and absorbed into polyacrylic acid and polyacrylamide copolymer particles. The particles were exposed to the chlorine gas using an acidified hypochlorite solution (bleach) as a source. The sodium chlorite polymer particles turned greenish yellow in color indicating that the chlorine gas could be absorbed by the particles and that the chlorite present in the polymer particles was available for chlorine dioxide gas generation. The particles were stable and retained their color in the chlorine gas atmosphere for many months.

Example 9

Direct Loading OF ClO2 Gas into Particles

Tap water was absorbed into polyacrylic acid and polyacrylamide copolymer particles. The particles were then exposed to chlorine dioxide vapors generated in a separate container, by the reaction of aqueous solutions of sodium chlorite and hydrochloric acid. The polymer particles became yellow in color indicating chlorine dioxide gas solubility in the particles. Particles were stable for many months.

Example 8

Delivery of ClO2 and Uptake of Heavy Metals

Chlorine dioxide gas containing particles prepared in Example 4 were transferred into a small volume of aqueous solution containing copper ion. Upon transfer of the particles the solution turned yellowish green. Additionally, the polymer particles turned green-blue in color indicating adsorption of copper ions by the polymer. This example provides an example of simultaneous gas delivery to a solution and heavy metal uptake by the polymer. This material characteristic is beneficial in many water treatment and purification applications.

Example 9

ClO2 Precursor Storage and Boric Acid

Sodium chlorite solution was absorbed into dry sodium hydroxide containing polyacrylic and polyacrylamide containing polymer particles. The hydroxide containing particles were previously prepared by absorbing a concentrated sodium hydroxide solution and drying. The solution pH of the chlorite containing particles was highly alkaline (pH>10). The particles were then placed in a sealed plastic bag. The particles were stable and uncolored. When several particles were exposed to tap water acidified with boric acid, the solution immediately became yellow in color.

Example 10

Electrochemical Generation of ClO2

A sodium chlorite particulate material was prepared with tap water and polyacrylic acid particles and polyacrylamide copolymer particles. The particles were then placed in a single container which also contained two platinum electrodes connected to a dc power source (type C battery). Shortly after connecting the power supply the polymer particles became green-yellow in color and a chlorine odor was detected above the container. This example indicates that the polymer particles containing solutions of chlorite can undergo direct electrochemical reaction to produce chlorine dioxide gas which is both retained and released by the polymer particles. Those experienced with electrochemical devices will understand that solar and ac power sources are suitable for use with the materials of the invention.

Example 11

Secondary Solution Preparation

A solution of chlorine dioxide was prepared by mixing hydrochloric acid with sodium chlorite in tap water. After formation of a yellow colored solution with a strong chlorine odor, polyacrylic acid and polyacrylamide copolymer particles were introduced. The particles rapidly absorbed the solution containing dissolved chlorine dioxide gas. The particles were stable and retained the yellow color for many weeks. When 5-10 individual particles were transferred to a one liter container of water, the chlorine dioxide concentration was determined to be approximately 1 ppm, using a DPD chlorine test kit.

Example 12

Polycarbonate Storage Materials

A solution of chlorine dioxide, yellow in color, was prepared by mixing aqueous solutions of chlorite and hydrochloric acid. This solution was used to fill a transparent polycarbonate container. The container was sealed and stored for several days. After removing the chlorine dioxide solution, the polycarbonate container retained a yellow color. The empty container was placed in a refrigerator with an unpleasant odor. After several minutes the unpleasant odor was not longer detected. The polycarbonate container slowly lost all yellow color over a period of weeks when exposed to the atmosphere.

The invention claimed is:

1. A composition for the generation and storage of a reactive gas consisting of:
    one or more particles consisting of one or more super-absorbent polymers, and
    a solvent containing one or more dissolved reactive gas precursors, wherein the solvent is absorbed to the one or more super-absorbent polymers, and
    at least one or more of an inhibiting chemical agent able to stabilize the generation of the reactive gas, a suspended agent, and a dissolved agent, wherein the inhibiting chemical agent is a base.

2. The composition of claim 1, wherein the reactive gas precursors are selected from a cation, inorganic acid, organic acid, oxidation agent, reduction agent, base, anion, soluble salt, and combinations thereof.

3. The composition of claim 2, wherein the anion is selected from a chlorite, chlorate, sulfite, bisulfite, sulfide, sulfate, carbonate, bicarbonate, cyanide, hypochlorite, nitrite, nitrate, hydroxide, chloride, bromide, iodide, and fluoride anion.

4. The composition of claim 2, wherein the oxidizing agent is selected from hypochlorite, hypochlorous acid, ozone, peroxide, and monopersulfate.

5. The composition of claim 1, wherein the gas is a halogen-containing gas, a carbon containing gas, an oxygen-containing gas, a phosphorous-containing gas, a sulfur-containing gas, or a nitrogen-containing gas.

6. The composition of claim 5, wherein the gas is chlorine, bromine, iodine, carbon dioxide, oxygen, nitrogen, sulfur dioxide, hydrogen sulfide, hydrogen cyanide, chlorine monoxide, chlorine dioxide, nitrogen monoxide, and nitrogen dioxide.

7. The composition of claim 1, wherein the solvent is a polar liquid, a non-polar liquid, or a combination thereof.

8. The composition of claim 1, wherein the one or more particles is a liquid absorber incorporating natural or synthetic polymers of organic, inorganic, or combined origin.

9. The composition of claim 1, wherein the particle is a liquid absorber incorporating natural or synthetic minerals.

10. The composition of claim 1, wherein the one or more super-absorbent polymers is a polyacrylic acid, a polyacrylamide or a copolymer thereof.

11. The composition of claim 1, wherein the composition is packaged in a gas permeable packaging material that allows gas transport but not liquid transport.

12. The composition of claim 1 wherein the composition comprises a gas concentration high enough to impart color to the composition.

13. The composition of claim 1, wherein the suspended agent comprises polycarbonate, polycarbonate derivatives, or combinations thereof.

14. The composition of claim 1, wherein a first reactive gas precursor is selected from a cation, inorganic acid, organic acid, and oxidation agent, and a second reactive gas precursor is selected from a reduction agent, base, anion, and soluble salt.

* * * * *